United States Patent [19]

Powers

[11] Patent Number: 4,659,855
[45] Date of Patent: Apr. 21, 1987

[54] ARYL SULFONYL FLUORIDE COMPOUNDS

[75] Inventor: James C. Powers, Atlanta, Ga.

[73] Assignee: Georgia Tech Research Corporation, Atlanta, Ga.

[21] Appl. No.: 493,064

[22] Filed: May 9, 1983

[51] Int. Cl.⁴ .................. C07C 141/14; C07C 143/70
[52] U.S. Cl. .................................. 558/23; 260/543 F; 560/9; 560/11; 560/12; 560/13; 560/14; 560/15; 560/16; 560/17; 560/18; 560/19; 560/25; 560/29; 560/32; 560/33; 560/38; 560/39; 560/43; 560/45; 560/51; 560/53; 560/55; 560/60; 560/61; 560/64; 560/73; 560/106; 560/109; 560/227; 558/24; 558/25; 558/26; 558/29; 558/30; 558/31; 558/32; 558/33; 558/34; 558/37; 558/44; 558/46; 558/47; 558/48; 558/49; 558/50; 558/51; 558/52; 558/56; 558/58; 558/250; 558/251; 558/252; 558/253; 558/254; 558/255; 558/256; 558/257; 558/260; 558/262; 558/263; 558/264; 558/265; 558/266; 558/267; 558/268; 558/269; 558/270; 558/276; 558/277

[58] Field of Search ............. 260/543 F, 543 R; 560/9, 11, 12, 13, 14, 15, 16, 17, 18, 19, 25, 29, 32, 33, 38, 39, 43, 45, 51, 53, 55, 60, 61, 64, 73, 106, 109, 227; 558/23, 24, 25, 26, 29, 30, 31, 32, 33, 34, 37, 44, 46, 47, 48, 49, 50, 51, 52, 56, 58, 250, 251, 252, 253, 254, 255, 256, 257, 260, 262, 263, 264, 265, 266, 267, 268, 269, 270, 276, 277

[56] References Cited

U.S. PATENT DOCUMENTS 3,186,847 6/1965 Willems et al. ................ 260/543 F

OTHER PUBLICATIONS

Gerig, J. T. et al., *J. Am. Chem. Society*, vol. 96 (1974), pp. 233–238.
Baker, B. R. et al., *J. Med. Chemistry*, (1969), pp. 118–122.
Lively, Mark O. et al., *Biochimica et Biophysica Acta*, vol. 525 (1978), pp. 171–179.
Yoshimura, Toshiaki et al., *J. Biological Chemistry*, vol. 257 (1982), pp. 5077–5083.

*Primary Examiner*—Natalie Trousof
*Assistant Examiner*—L. Hendriksen
*Attorney, Agent, or Firm*—Newton, Hopkins & Ormsby

[57] ABSTRACT

Certain novel aryl sulfonyl fluorides, their preparation, and their use in inhibiting serine proteases with chymotrypsin-like and elastase-like specificity.

3 Claims, No Drawings

ARYL SULFONYL FLUORIDE COMPOUNDS

BACKGROUND OF THE INVENTION

Selective and reactive protease inhibitors are widely used in biomedical research. They are used to identify the nature of new proteolytic enzymes encountered in isolation and characterization studies. They are also used both in research and industrially to prevent undesired proteolysis of proteins and peptides during the production, isolation, purification, transport and storage of these valuable materials. They could also be used industrially to increase the yields of proteins and peptides produced by cloning or fermentation by inhibiting proteolysis of the products due to proteases released by the parent organism or by contaminating organisms in the growth medium. Protease inhibitors could also be used to protect proteins and peptides during storage or use from proteolysis which would destroy or alter the activity and/or function of the peptides or proteins. Such uses would include their addition to antibodies, enzymes, plasma proteins or other proteins which are widely sold for use in clinical analysis, biomedical research, therapy, and for many other reasons.

Serine proteases are the most widely distributed class of proteolytic enzymes. Serine proteases can be further divided into three main classes based on their substrate specificity: chymotrypsin-like, elastase-like, and trypsin-like. In addition, there are a few other serine proteases which do not fit into any of the above three groups. This invention relates only to chymotrypsin-like and elastase-like enzymes. Chymotrypsin and chymotrypsin-like enzymes normally cleave peptide bonds in proteins and peptides where the amino acid residue on the carbonyl side of the split bond ($P_1$ residue) is typically Trp, Tyr, Phe, Met, Leu or other amino acid residues which contain aromatic or large alkyl side chains. Elastase and elastase-like enzymes, on the other hand, cleave peptide bonds where the $P_1$ amino acid residue is much smaller, typically Ala, Val, Ser, Leu and other similar amino acids. All of the above enzymes have extensive secondary specificity and recognize amino acid residues removed from the $P_1$ residue. Chymotrypsin-like and elastase-like enzymes are widely distributed. They are found in leukocytes (white blood cells), mast cells, pancreatic juice, and many other cell types and fluids in higher organisms. They are also secreted by many types of bacteria, yeast, viruses and parasites. These enzymes can be very destructive if not properly controlled. Thus there is a need for selective and reactive inhibitors for these enzymes.

Sulfonyl fluorides have been widely used as inhibitors of serine proteases since their intial discovery by Fahrney and Gold (cf. J. Am. Chem. Soc. 85, pp. 997–1000 (1963)). These reagents, which are fairly stable in aqueous solution, inhibit serine proteases by sulfonylation of the active site serine residue to give a stable sulfonyl enzyme derivative. Sulfonyl fluorides have been shown to inhibit most serine proteases including chymotrypsin (cf. Baker and Hurlbut, J. Med. Chem., 12, pp 118–122 (1969)), trypsin, elastase, and complement, coagulation, and fibrinolytic serine proteases. However, sulfonyl fluorides are not usually considered to be highly specific and in fact phenylmethanesulfonyl fluoride is usually considered to be a fairly general inhibitor of serine proteases. Lively and Powers showed that the specificity of sulfonyl fluorides toward elastase, cathepsin G and chymotrypsin could be improved with structural changes in the inhibitor (cf. Biochim. Biophys. Acta 525, pp 171–179(1978)). While a difference in rate of 26,000 fold was observed between the fastest and slowest inhibitor, the absolute reactivities of the inhibitors were comparatively slow. It is an object of this invention to find a novel group of aryl sulfonyl fluorides which will rapidly and selectively inhibit elastase-like and chymotrypsin-like enzymes.

DETAILED DESCRIPTION OF THE INVENTION

Certain aryl sulfonyl fluorides have been found to selectively inhibit elastase by blocking the active site of the enzyme by sulfonylation of the enzyme's active site serine residue. The inhibition reaction occurs very rapidly. The novel aryl sulfonyl fluoride elastase inhibitors have the following structural formula:

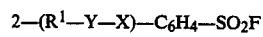

$$2\text{---}(R^1\text{---}Y\text{---}X)\text{---}C_6H_4\text{---}SO_2F$$

wherein

X is selected from the group consisting of NH, O, S, $CH_2$, and $CF_2$ (but not larger groups such as $NCH_3$, nor groups such as $NSO_2CF_3$ which have more than 2 atoms other than hydrogen or fluorines).

Y is selected from the group consisting of CO, S, SO, O, $CF_2$, NH, and $CH_2$ (but not larger groups such as $SO_2$ or $—C(OCH_3)=$ which contain 3 or more atoms other than hydrogen or a halide).

$R^1$ is a $C_{1-5}$ fluoroalkyl (such as $CF_3$, $CF_2CF_3$, or $CF_2CF_2CF_3$, but not longer or more bulky groups such as $CF_3CO—Ala$, $CF_3(CF_2)_6$, $CF_3CONH(CH_2)_5$, or $C_6F_5$).

The $R^1$ group must be a perfluoroalkyl and not an alkyl group, and could be branched. Substitution of a few of the fluorine atoms in the perfluoroalkyl group for hydrogens or other halides will not significantly alter the capacity of the sulfonyl fluoride to inhibit elastase. One or two of the carbons in the perfluoroalkyl group could be replaced by O, S, NH, or $CH_2$ as long as the $R^1$ group maintains its fluorocarbon and hydrophobic character. When $R^1$ is a $C_{4-5}$ perfluoroalkyl, the sulfonyl fluoride is also an inhibitor of chymotrypsin-like enzymes.

The substituents on the aromatic ring must be ortho to each other and not meta or para. The aromatic ring could be replaced by heterocyclic rings such as a pyridine ring or a thiadiazole ring. The $—C_6H_4—$ could be replaced by a cis double bond or substituted double bond such as $—CH=CH—$, $—CMe=CH—$, $—CMe=CMe—$ (Me=methyl), or $—CCF_3=CCF_3—$.

The following novel compounds are representative of the invention:

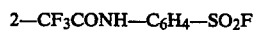

$$2\text{---}CF_3CONH\text{---}C_6H_4\text{---}SO_2F$$

$$2\text{---}CF_3CF_2CONH\text{---}C_6H_4\text{---}SO_2F$$

$$2\text{---}CF_3CF_2CF_2CONH\text{---}C_6H_4\text{---}SO_2F$$

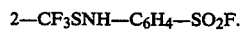

$$2\text{---}CF_3SNH\text{---}C_6H_4\text{---}SO_2F.$$

Another novel aryl sulfonyl fluoride elastase inhibitor of this invention has the following structural formula:

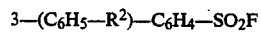

$$3\text{---}(C_6H_5\text{---}R^2)\text{---}C_6H_4\text{---}SO_2F$$

wherein $R^2$ is a linear group of 0.9 to 2.0 nm bridging the two aromatic rings. The $R^2$ group is composed of 6 to 13 small uncharged atomic groupings such as NH, CO, $CH_2$, $SO_2$, O, NH, S and $CF_2$. Ideal inhibitors are formed when $R^2$ has 8 or 11 atomic groupings. Suitable $R^2$ groups are —$CH_2$—O—CO—NH—$(CH_2)_2$—CO—NH— and

—$CH_2$—O—CO—NH—$(CH_2)_5$—CO—NH—.

The substituents on the aromatic ring must be meta to each other and not ortho or para. Both aromatic rings could contain substituents such as F, OMe, or $NO_2$. Both aromatic rings could be replaced by heterocyclic rings such as pyridine or thiadiazole rings.

The following novel compounds are representative of the invention:

3—$C_6H_5CH_2OCONH(CH_2)_2CONH$—$C_6H_4$—$SO_2F$

3—$C_6H_5CH_2OCONH(CH_2)_5CONH$—$C_6H_4$—$SO_2F$

Certain aryl sulfonyl fluorides have been found to selectively inhibit chymotrypsin-like enzymes such as bovine chymotrypsin, human cathepsin G, human skin chymase, rat mast cell chymase I and rat mast cell chymase II. The novel aryl sulfonyl fluorides of this invention have the following structural formula:

2—$(C_6H_5$—$R^3)$—$C_6H_4$—$SO_2F$ wherein $R^3$ is a linear spacing group of 0.45 to 1.7 nm bridging the two aromatic rings. The $R^3$ group is composed of 3 to 11 small uncharged atomic groupings such as NH, CO, $CH_2$, $CF_2$, $SO_2$, O, NH, and S. Suitable spacing groups are —$CH_2OCONH(CH_2)_n CONH$— with n=1, 2, or 5. If n=2 or 5 the inhibitor is very selective toward human skin chymase. Another suitable spacing group is $CONHCH_2CONH$. Another suitable spacing grouping is —$CH_2NHCONH$— and the inhibitor is very selective toward mast cell chymase.

The substituents on the second aromatic ring must be ortho to each other and not meta or para. Both aromatic rings could contain substituents such as F, OMe, or $NO_2$. Both aromatic rings could be replaced by heterocyclic rings such as pyridine or thiadiazole.

The following novel compounds are representative of the invention:

2—$C_6H_5CH_2$—O—CO—NH$(CH_2)CONH$—$C_6H_4$—$SO_2F$

2—$C_6H_5CH_2$—O—CO—NH$(CH_2)_2$—CONH—$C_6H_4$—$SO_2F$

2—$C_6H_5CH_2$—O—CO—NH$(CH_2)_5$—CONH—$C_6H_4$—$SO_2F$

2—$C_6H_5CONHCH_2CONH$—$C_6H_4$—$SO_2F$

2—$C_6H_5CH_2NHCONH$—$C_6H_4$—$SO_2F$

To use the above identified inhibitors, they are dissolved in an organic solvent such as dimethylsulfoxide or ethanol and are added to an aqueous solution containing the protease which is to be inhibited such that the final concentration of organic solvent is 25% or less. The inhibitors may also be added as solids or in suspension. The final concentration of the inhibitor in the inhibition solution should be at least equal to that of the protease or proteases in the solution. However, more complete and faster inhibition will be obtained if an inhibitor concentration of 10 to 1000 fold higher than the protease(s) concentration is used. The time required for complete inhibition will be dependent on the concentration of inhibitor used, but can be calculated from the measured rates of inhibition (cf. Yosimura, Barker, and Powers, J. Biol. Chem., 257, pp 5077–5084 (1982)).

The following examples are given to illustrate the invention and are not intended to limit it in any manner.

EXAMPLE 1

Preparation of 2—$(CF_3CF_2CONH)$—$C_6H_4$—$SO_2F$

Pentafluoropropionic anhydride (2 ml) was added to 1 g of 2—$NH_2$—$C_6H_4$—$SO_2F$. The mixture was stirred for 10 min after completion of the exothermic reaction and then poured into ice water. The precipitate was filtered and recrystallized from methanol-water yielding 0.93 g of a white solid with mp 70 deg centigrade. Anal. Calcd. for $C_9H_5F_6NO_3S$: C, 33.66; H, 1.57; N, 4.36; S, 9.98. Found: C, 33.72, H, 1.62; N, 4.46; S, 9.94.

EXAMPLE 2

Preparation of 2—$(C_6H_5CH_2O$—CO—$NHCH_2CONH)$—$C_6H_4$—$SO_2F$

To a stirred solution of 1.6 g of 2—$NH_2$—$C_6H_4$—$SO_2F$ in 40 ml of pyridine cooled to −20 deg centigrade was added dropwise 0.40 ml of $PCl_3$. The solution was stirred for 45 min at −20 and then warmed to room temperature. $C_6H_5CH_2OCONHCH_2CO_2H$ (1.9 g) was added and the reaction refluxed for 3 hrs. The product was purified on a silica gel column by elution with 3% ethyl acetate-benzene. The oily product was triturated with ether yielding 0.745 g of a white solid with mp 110–112. Anal. Calcd. for $C_{16}H_{15}FN_2O_5S$: C, 52.46;, H, 4.098; N, 7.65. Found: C, 52.72; H, 4.14; N, 7.59.

Other illustrative examples are incorporated by reference herein in the Yoshimura, Barker and Powers publication (cf. J. Biol. Chem. 257, pp 5077–5084(1982)). The applicant was the director of the research coauthored by others.

What is claimed is:

1. A compound of the formula:

2—$(R^1$—Y—X)—$C_6H_4$—$SO_2F$ wherein
X is selected from the group consisting of NH, O, S, and $CF_2$,
Y is selected from the group consisting of CO, S, SO, O, $CF_2$, NH, and $CH_2$, and
$R^1$ is a $C_{1-5}$ perfluoroalkyl.

2. A substituted diphenyl compound of the formula:

3—$(C_6H_5$—$R^2)$—$C_6H_4$—$SO_2F$ wherein $R^2$ is linear group of 0.9 to 2.0 nm bridging the two phenyl rings and is composed of 6 to 13 uncharged atomic groupings selected from the group consisting of CO, $CH_2$, O, NH, S, and $CF_2$.

3. A substituted diphenyl compound of the formula:

2—$(C_6H_5$—$R^3)$—$C_6H_4$—$SO_2F$ wherein $R^3$ is a linear spacing gorup of 0.45 to 1.7 nm bridging the two phenyl rings and is composed of 3 to 11 uncharged atomic groupings selected from the group consisting of CO, $CH_2$, $CF_2$, $SO_2$, O, NH, and S.

* * * * *